(12) United States Patent
Biberger

(10) Patent No.: US 11,521,475 B1
(45) Date of Patent: Dec. 6, 2022

(54) SYSTEM FOR AND METHOD REMOTELY MONITORING CHEMISTRY OF RECREATIONAL WATER FACILITIES

(71) Applicant: Hitek Aqua Systems, Tempe, AZ (US)

(72) Inventor: Maximilian A. Biberger, Scottsdale, AZ (US)

(*) Notice: Subject to any disclaimer, the term of this patent is extended or adjusted under 35 U.S.C. 154(b) by 0 days.

(21) Appl. No.: 15/253,555

(22) Filed: Aug. 31, 2016

Related U.S. Application Data

(60) Provisional application No. 62/212,437, filed on Aug. 31, 2015.

(51) Int. Cl.
*G01N 33/18* (2006.01)
*G08B 21/18* (2006.01)

(52) U.S. Cl.
CPC ............ *G08B 21/182* (2013.01); *G01N 33/18* (2013.01)

(58) Field of Classification Search
CPC .. G01N 33/18; G01N 33/1886; G01N 27/302; C02F 1/008; G08B 21/182; G06T 7/408
See application file for complete search history.

(56) References Cited

U.S. PATENT DOCUMENTS

| | | |
|---|---|---|
| D138,325 S | 7/1944 | Pool |
| 3,162,470 A | 12/1964 | Davidson et al. |
| D242,618 S | 12/1976 | Milo |
| D254,266 S | 2/1980 | Tableriou |
| 4,435,095 A | 3/1984 | Jones et al. |
| 4,510,487 A | 4/1985 | Wolfe et al. |
| 4,781,810 A | 11/1988 | Tucker |
| 4,900,432 A | 2/1990 | Arnold et al. |
| 4,940,946 A | 7/1990 | Nazaryan |
| 5,055,183 A | 10/1991 | Buchan |

(Continued)

FOREIGN PATENT DOCUMENTS

| | | |
|---|---|---|
| DE | 19951436 A1 | 11/2000 |
| EP | 821514 A1 | 1/1998 |

(Continued)

OTHER PUBLICATIONS

Griffin, William R., "Maintaining Swimming Pools, Spas, Whirlpool Tubs, and Saunas", Jan. 2001, Cleaning Consultant Services, Inc., Seattle WA, 4 pages.

(Continued)

*Primary Examiner* — An T Nguyen
(74) *Attorney, Agent, or Firm* — Haverstock & Owens, A Law Corporation

(57) ABSTRACT

A sensor pod is used to analyze one or more chemistry values of a recreational water facility such as a pool, a hot tub and a sauna. The sensor pod can sense one or more chemistry values such as pH, alkalinity, calcium hardness, chlorine levels, and cyanuric acid levels. The sensor pod uploads the one or more chemistry values to a server. The chemistry values are processed and analyzed at the server against a set of target or ideal level values to obtain a set of output chemistry values and based upon the output values a message is sent to a customer. The message can instructs the customer to apply remedial steps to normalize the chemistry values as needed. The message can instruct the customer and/or a pool owner to apply remedial steps to normalize the chemistry values as needed.

7 Claims, 3 Drawing Sheets

(56) References Cited

U.S. PATENT DOCUMENTS

| | | | |
|---|---|---|---|
| 5,115,222 A | | 5/1992 | Peralta et al. |
| 5,124,960 A | | 6/1992 | Miller et al. |
| 5,152,610 A | | 10/1992 | Hallett |
| 5,169,236 A | | 12/1992 | Iest |
| 5,189,350 A | | 2/1993 | Mallett |
| 5,422,014 A | | 6/1995 | Allen et al. |
| 5,518,635 A | | 5/1996 | Kohlman |
| D371,824 S | | 7/1996 | Price et al. |
| 5,681,110 A | | 10/1997 | Burzacchi |
| 5,788,826 A | | 8/1998 | Nyberg |
| 5,996,138 A | | 12/1999 | Kentch |
| 6,113,858 A | | 9/2000 | Tang et al. |
| D432,206 S | | 10/2000 | Stoltz et al. |
| D439,313 S | | 3/2001 | Wey et al. |
| 6,223,359 B1 | | 5/2001 | Oltmanns et al. |
| 6,225,900 B1 | | 5/2001 | Keon et al. |
| 6,228,272 B1 | | 5/2001 | Gola |
| 6,238,553 B1 | | 5/2001 | Lin |
| 6,294,086 B1 | | 9/2001 | Reeves |
| 6,309,538 B1 | | 10/2001 | Khan |
| 6,340,431 B2 | | 1/2002 | Khan |
| 6,476,721 B1 | | 11/2002 | Diebold |
| 6,579,446 B1 | | 6/2003 | Teran et al. |
| 6,653,842 B2 | | 11/2003 | Mosley et al. |
| 6,697,706 B2 | | 2/2004 | Gardner, Jr. |
| 6,713,298 B2 | | 3/2004 | McDevitt et al. |
| D489,431 S | | 5/2004 | Antunez |
| 6,792,956 B2 | | 9/2004 | Bredo et al. |
| 6,958,693 B2 | | 10/2005 | Rothgeb et al. |
| 7,037,038 B1 | | 5/2006 | Haski et al. |
| D526,382 S | | 8/2006 | Thompson |
| D537,913 S | | 3/2007 | Biberger et al. |
| D559,943 S | | 1/2008 | Mercer |
| 9,776,888 B1 * | | 10/2017 | Kurani ................. C02F 1/008 |
| 2001/0045380 A1 | | 11/2001 | Khan |
| 2002/0035403 A1 * | | 3/2002 | Clark ................. G05B 23/027 |
| | | | 700/19 |
| 2003/0227394 A1 | | 12/2003 | Rothgeb et al. |
| 2004/0031329 A1 | | 2/2004 | Carpenter et al. |
| 2004/0066313 A1 | | 4/2004 | Ong et al. |
| 2004/0208499 A1 | | 10/2004 | Grober et al. |
| 2005/0220169 A1 | | 10/2005 | McGowan-Scanlon |
| 2005/0225766 A1 | | 10/2005 | Hansen et al. |
| 2005/0279677 A1 | | 12/2005 | Lin |
| 2006/0092008 A1 * | | 5/2006 | Corrington ......... G08B 26/007 |
| | | | 340/505 |
| 2006/0096927 A1 | | 5/2006 | Clukies |
| 2006/0292043 A1 * | | 12/2006 | Biberger ................ G01N 33/18 |
| | | | 73/53.01 |
| 2007/0160498 A1 * | | 7/2007 | Biberger ................ G01N 33/18 |
| | | | 422/68.1 |
| 2008/0039977 A1 * | | 2/2008 | Clark ................. G05D 23/1905 |
| | | | 700/282 |
| 2012/0133508 A1 * | | 5/2012 | Stebe ..................... G06Q 10/00 |
| | | | 340/540 |
| 2012/0158336 A1 * | | 6/2012 | Duchamp ............... C02F 1/008 |
| | | | 702/81 |
| 2014/0000507 A1 * | | 1/2014 | Clark .................... G01N 21/77 |
| | | | 116/206 |
| 2015/0160178 A1 * | | 6/2015 | Lee ..................... G01N 27/302 |
| | | | 73/61.43 |
| 2015/0310634 A1 * | | 10/2015 | Babcock .................. G06T 7/90 |
| | | | 702/85 |
| 2016/0052798 A1 * | | 2/2016 | Downs .................... B01J 49/75 |
| | | | 210/85 |
| 2016/0096742 A1 * | | 4/2016 | Mori ....................... C02F 1/008 |
| | | | 702/188 |
| 2016/0131608 A1 * | | 5/2016 | Howes, Jr. ........... G01N 33/182 |
| | | | 324/693 |
| 2017/0212536 A1 * | | 7/2017 | Potucek ................ G05D 7/0629 |
| 2017/0336381 A1 * | | 11/2017 | Zeevi .................... A01K 63/04 |

FOREIGN PATENT DOCUMENTS

| | | | | |
|---|---|---|---|---|
| GB | 2365122 A | | 2/2002 | |
| WO | WO-0239107 A1 * | | 5/2002 | ......... G01N 33/1886 |
| WO | 03012434 A2 | | 2/2003 | |
| WO | 2003087501 A1 | | 10/2003 | |
| WO | 2003091668 A2 | | 11/2003 | |
| WO | 2004019295 A1 | | 3/2004 | |
| WO | 2005008443 A2 | | 1/2005 | |

OTHER PUBLICATIONS

"Water Chemistry for Swimming Pools," Pool Water Chemistry, North Carolina Department of Environment and Natural Resources, available on the Internet archive at <http://www.deh.enr.state.nc.us/ehs/chem.htm>, Dec. 19, 2002, 12 pages.

Egles, David, "Ranger 1: A Self-Propelled Data Buoy", Oceans San Diego Conference, Ocean Engineering and the Environment, I.E.E.E. US, Nov. 12, 1985, vol. 1, 6 pages.

Supplementary European Search Report, European Patent Office, EP 06 78 5530, dated Dec. 16, 2016, 11 pages.

* cited by examiner

SYSTEM FOR AND METHOD REMOTELY MONITORING CHEMISTRY OF RECREATIONAL WATER FACILITIES

RELATED APPLICATIONS

This application claims priority of U.S. provisional application Ser. No. 62/212,437, filed Aug. 31, 2015, and entitled "WiFi/APP POOL WATER SENSOR," which is incorporated herein by reference.

FIELD OF THE INVENTION

The present invention is generally directed to recreational water facilities. More specifically, the present invention is directed to monitoring and controlling water chemistries in recreational water facilities.

BACKGROUND OF THE INVENTION

In recreational water facilities such as pools, spas, and hot tubs, water chemistry must be properly balanced. Water chemistry imbalances, however slight, can pose health and maintenance risks. Swimmers can be exposed to dangerous amounts of bacteria when pH values are too high and to eye and skin irritants when pH values are too low. Structures, such as circulation equipment, sanitation components, and pool surfaces can be corroded and otherwise damaged; repairs can be costly and time consuming. To reduce these risks, water chemistry must be properly monitored and maintained within predetermined levels.

SUMMARY OF THE INVENTION

A sensor pod is used to analyze one or more chemistry values of a recreational water facility such as a pool, a hot tub and a sauna. The sensor pod can sense one or more chemistry values such as pH, alkalinity, calcium hardness, chlorine levels, and cyanuric acid levels. The sensor pod uploads the one or more chemistry values to a server. The chemistry values are processed and analyzed at the server against a set of target or ideal level values to obtain a set of output chemistry values and based upon the output values a message is automatically sent to a customer. The message can instruct the customer and/or a pool owner to apply remedial steps to normalize the chemistry values as needed.

In one aspect, a water chemistry monitoring system for a recreational water facility comprises a water chemistry sensor for sensing one or more chemistry values of the recreational water facility, a server configured for receiving the one or more chemistry values sensed by the sensor and comparing the values against a set of target chemistry values at the server to obtain a set of output chemistry values, and a transmitter that automatically sends a message to a customer based upon the output chemistry values. In some embodiments, the one or more chemistry values comprise one or more of pH, alkalinity, calcium hardness, chlorine levels, cyanuric acid, and temperature. In some embodiments, the message comprises a message indicating the one or more chemistry output chemistry values are within the targeted range. Alternatively, the message comprises a message indicating the one or more chemistry output chemistry values are not within the targeted range. In some embodiments, the message comprises one or more recommended remedial steps. In some embodiments, the message is sent to a customer's smart device.

In a further aspect, a method of monitoring the water chemistry of a recreational water facility, the method comprising sensing one or more water chemistry values of the recreational water facility, uploading the one or more chemistry values to a server, analyzing the one or more chemistry values, and based upon the one analyzed chemistry values, sending a message to a customer with a specific recommendation. In some embodiments, the one or more chemistry values comprise one or more of pH, alkalinity, calcium hardness, chlorine levels, cyanuric acid, and temperature. The one or more sensed chemistry values are analyzed against a set of target chemistry values. In some embodiments, the message comprises a message indicating the one or more chemistry output chemistry values are within the targeted range. Alternatively, the message comprises a message indicating the one or more chemistry output chemistry values are not within the targeted range. In some embodiments, the message comprises one or more recommended remedial steps. In some embodiments, the message is sent to a customer's smart device.

BRIEF DESCRIPTION OF THE DRAWINGS

Several example embodiments are described with reference to the drawings, wherein like components are provided with like reference numerals. The example embodiments are intended to illustrate, but not to limit, the invention. The drawings include the following figures.

DETAILED DESCRIPTION OF THE EMBODIMENTS

Embodiments of the invention are directed to a sensor pod in cooperation with a remotely located server used to analyze one or more chemistry values of a recreational water facility such as a pool, a hot tub and a sauna. The sensor pod can sense one or more chemistry values such as pH, alkalinity, calcium hardness, chlorine levels, and cyanuric acid levels. The sensor pod uploads the one or more chemistry values to a server. The chemistry values are processed and analyzed at the server against a set of target or ideal level values to obtain a set of output chemistry values and based upon the output values a message is sent to a customer. The message can instruct the customer to apply remedial steps to normalize the facility's chemistry values as needed.

Reference will now be made in detail to implementations of system for and method of remotely monitoring the chemistry of recreational water facilities as illustrated in the accompanying drawings. The same reference indicators will be used throughout the drawings and the following detailed description to refer to the same or like parts. In the interest of clarity, not all of the routine features of the implementations described herein are shown and described. It will be appreciated that in the development of any such actual implementation, numerous implementation-specific decisions can be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
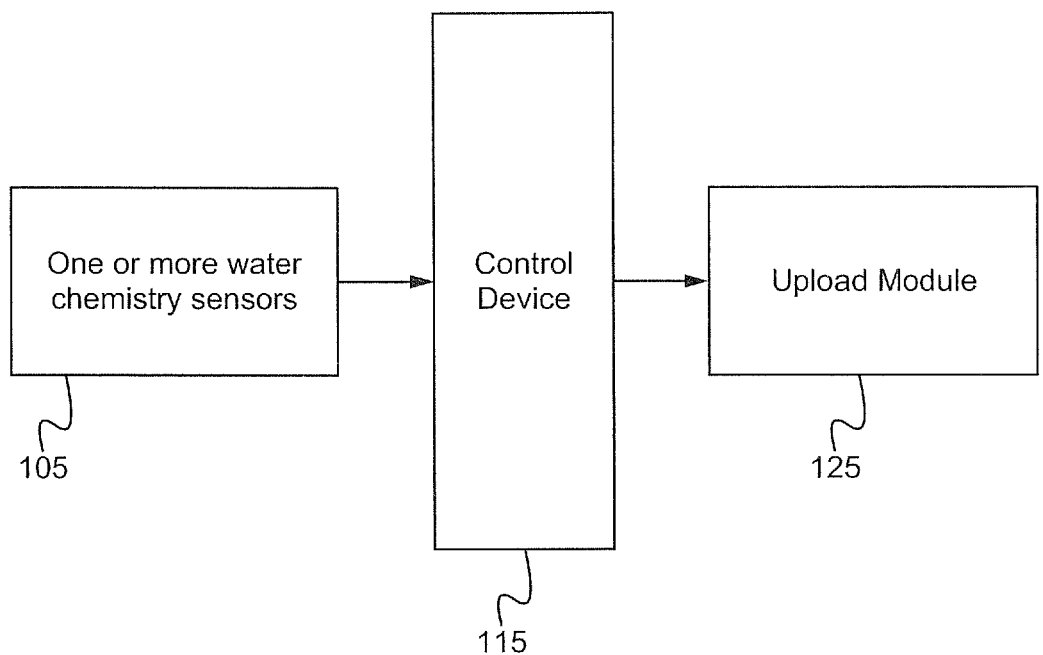
FIG. 1 illustrates a schematic view of a water chemistry sensor, in accordance with some embodiments.

Referring now to FIG. 1, a water chemistry sensor or sensor pod 100 is depicted therein. As shown within FIG. 1, the water chemistry sensor 100 comprises one or more water chemistry sensors 105 for sensing one or more chemistry values of the recreational water facility, a control device 115 and an upload module 115. The control device 115 receives a signal from the one or more water chemistry sensors 105 and sends a signal to the upload module 125 which uploads water chemistry data to a remote location. For example, in some embodiments, the upload module 125 is configured to upload water chemistry data to a remotely located server. In some embodiments, the one or more chemistry sensors 105 are configured to sense one or more of pH, alkalinity, calcium hardness, chlorine levels, and cyanuric acid levels. Additionally, in some embodiments, the one or more water chemistry sensors 105 are also configured to sense a water temperature of the recreational water facility. In some embodiments, the recreational water facility comprises a pool, a hot tub or a sauna.

In some embodiments, the upload module 125 is configured to upload one or more of the chemistry values to a remotely located server. For example, in some embodiments, the upload module 125 uploads the one or more chemistry values to a server located at a remote storage facility. In some embodiments, the one or more sensed chemistry values are processed and analyzed at the server. Specifically, the one or more sensed chemistry values are compared against a set of target or ideal level values to obtain a set of output chemistry values and based upon the output values a message is sent to a customer. For example, in some embodiments, if the one or more sensed chemistry values are equal to the target or ideal level values, then a message is sent to the customer that the chemistry of the pool is okay and that changes are not needed. Alternatively, in some embodiments, if the one or more sensed chemistry values are not within the threshold values, then a message is sent to the customer that the chemistry of the pool is not okay and that changes are needed. If the one or more sensed chemistry values, are not okay, then the server can send a message to the customer along with recommendations with remedial steps.

In some embodiments, the server sends the message to a device of the customer, such as a smart phone, tablet, tablet PC, or PC. In some embodiments, the message is automatically sent to the customer. Alternatively, the customer can log into the server to obtain the output chemistry values and/or recommended remedial steps.

In some embodiments, the water chemistry sensor or sensor pod 100 comprises a floating device which floats on the water of the recreational water facility. Alternatively, in some embodiments, the water chemistry sensor or sensor pod 100 is embedded within a water or pump line of the recreational water facility. Particularly, the water chemistry sensor or sensor pod 100 can be located at any appropriately desired location of the recreational water facility. For example, in some embodiments, the water chemistry sensor or sensor pod 100 can be embedded within a pool sweep or a floating chemical dispenser of the recreational water facility. In some embodiments, the sensor pod 100 communicates with the remotely located sever by communicating with a wireless network such as a WiFi network. However, the sensor pod 100 can communicate with the server using any appropriately desired network.

Figure 2:
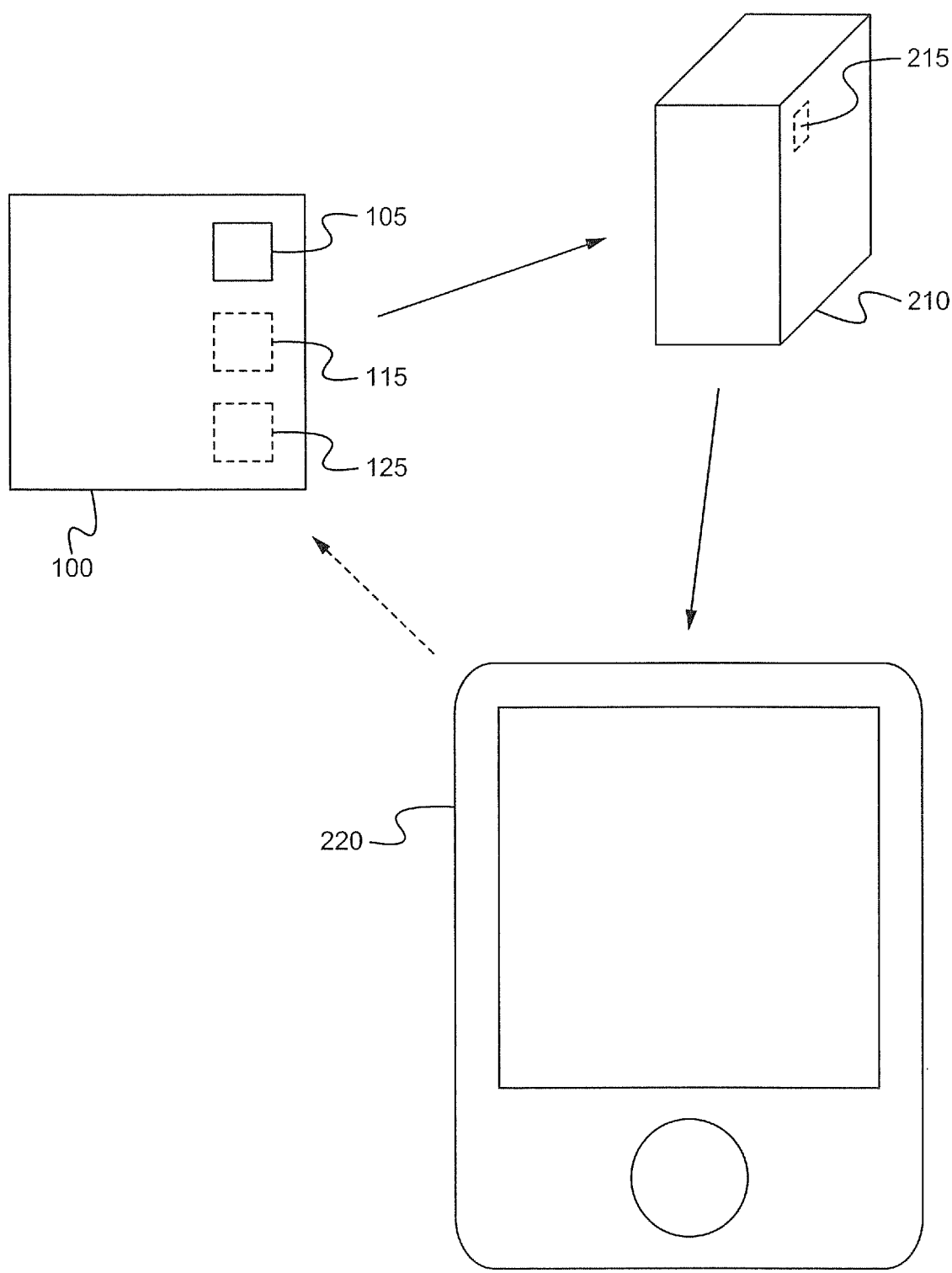
FIG. 2 illustrates a water chemistry monitoring system, in accordance with some embodiments.

Referring now to FIG. 2, a water chemistry monitoring system is depicted therein. The water chemistry monitoring system 200 comprises a water chemistry sensor or sensor pod 100 for sensing one or more chemistry values of a recreational water facility and a server 210 configured for receiving the one or more chemistry values sensed by the water chemistry sensor or sensor pod 100. As described above, in some embodiments, the water chemistry sensor 100 comprises one or more water chemistry sensors 105 for sensing one or more chemistry values of the recreational water facility, a control device 115 and an upload module 125. The control device 115 receives a signal from the one or more water chemistry sensors 105 and sends a signal to the upload module 125 which uploads water chemistry data to a remote location. The received chemistry values are processed and analyzed at the server 210 against a set of target chemistry values to obtain a set of output chemistry values. In some embodiments, the received chemistry values are stored to obtain a historical record of chemistry values for the recreational water facility. In some embodiments, the recreational water facility comprises a pool, a hot tub or a sauna.

As described above, the one or more sensed chemistry values are compared against a set of target or ideal level values to obtain a set of output chemistry values and based upon the output values a message is sent to an electronic device 220 of a customer. Particularly, after the chemistry values have been analyzed, a set of output chemistry values is automatically sent to the electronic device 220 by a transmitter 215 at the server 210.

In some embodiments, the electronic device comprises a smart phone, tablet, tablet PC, or PC. In some embodiments, the desired or target chemistry values are values set by the customer. Alternatively, the desired or target chemistry values are baseline values that can be set according to industry standard norms and procedures.

If the one or more sensed chemistry values are equal to the target or ideal level values, then a message is sent to the customer that the chemistry of the pool is okay and that changes are not needed. Alternatively, in some embodiments, if the one or more sensed chemistry values are not within the threshold values, then a message is sent to the customer that the chemistry of the pool is not okay and that changes are needed. If the one or more sensed chemistry values, are not okay, then the server can send a message to the customer along with recommendations with remedial steps. In some embodiments, the message is automatically sent to the customer. Alternatively, the customer can log into the server to obtain the output chemistry values and/or recommended remedial steps. Additionally, in some embodiments, the electronic device 220 communicates with the recreational water facility and/or the sensor pod 100 to implement the recommendations.

Figure 3:
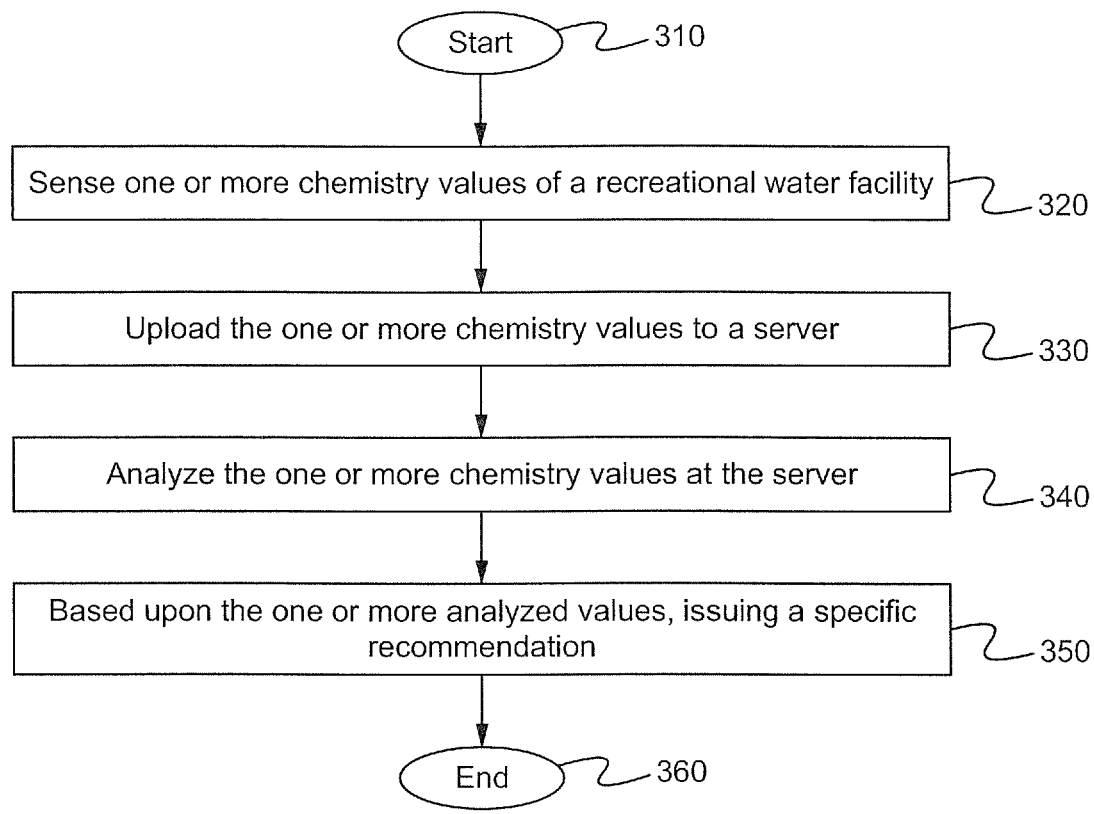
FIG. 3 illustrates a method of monitoring the water chemistry of a water facility, in accordance with some embodiments.

FIG. 3 illustrates a method of monitoring the water chemistry of a recreational water facility. The method begins in the step 310. In the step 320, one or more chemistry values are sensed and in the step 330, the one or more chemistry values are uploaded to a server. In some embodiments, the chemistry values comprise one or more of pH, alkalinity, calcium hardness, chlorine levels, and cyanuric acid levels. Then, in the step 340, the one or more sensed chemistry values are processed and analyzed at the server. In the step 350, one or more recommendations and/or recommended remedial steps is sent to a customer based upon the analyzed values.

As described above, the one or more sensed chemistry values are compared against a set of target or ideal level values to obtain a set of output chemistry values and based upon the output values a message is sent to an electronic device of a customer. In some embodiments, the electronic device comprises a smart phone, tablet, tablet PC, or PC. In some embodiments, the desired or target chemistry values are values set by the customer. Alternatively, the desired or target chemistry values are baseline values that can be set according to industry standard norms and procedures.

If the one or more sensed chemistry values are equal to the target or ideal level values, then a message is sent to the customer that the chemistry of the pool is okay and that changes are not needed. Alternatively, in some embodiments, if the one or more sensed chemistry values are not within the threshold values, then a message is sent to the customer that the chemistry of the pool is not okay and that changes are needed. If the one or more sensed chemistry values, are not okay, then the server can send a message to the customer along with recommendations with remedial steps. In some embodiments, the message is automatically sent to the customer. Alternatively, the customer can log into the server to obtain the output chemistry values and/or recommended remedial steps.

In operation, a sensor pod is used to analyze one or more chemistry values of a recreational water facility such as a pool, a hot tub and a sauna. The sensor pod can sense one or more chemistry values such as pH, alkalinity, calcium hardness, chlorine levels, and cyanuric acid levels. The sensor pod uploads the one or more chemistry values to a server. The chemistry values are processed and analyzed at the server against a set of target or ideal level values to obtain a set of output chemistry values and based upon the output values a message is sent to a customer. The message can instruct the customer to apply remedial steps to normalize the facility's chemistry values as needed. Particularly, the system and method as described herein enable a customer and a service to remotely monitor the chemistry of a recreational water facility to ensure that the chemistry values of the facility remain consistent and within the desired levels. Additionally, because the remedial message is sent directly to the customer, the customer is saved from having to call a technician or other service and can maintain the water facility themselves. Accordingly, the systems for and methods of remotely monitoring chemistry values of recreation facilities as described herein has many advantages.

The present invention has been described in terms of specific embodiments incorporating details to facilitate the understanding of the principles of construction and operation of the invention. Such references, herein, to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A remote water chemistry monitoring system for a recreational water facility comprising:
   a. a water chemistry sensor pod for sensing one or more chemistry values of water of the recreational water facility;
   b. a server that receives the one or more chemistry values sensed by the sensor pod, wherein the one or more chemistry values are uploaded to the server by the sensor pod and where the server compares the values against user set target chemistry values at the server to obtain output chemistry values; and
   c. a transmitter at the server that automatically sends first and second messages to a smart device based on the output chemistry values, wherein the first message indicates that the output chemistry values are within a targeted range, and the second message indicates that the output chemistry values are not within the targeted range and includes one or more remedial steps to be applied to the water to normalize the chemistry values, and wherein the sensor pod receives communications from the smart device to implement the remedial steps.

2. The chemistry monitoring system of claim 1, wherein the one or more chemistry values comprise one or more of pH, alkalinity, calcium hardness, chlorine levels, cyanuric acid, and temperature.

3. A method of monitoring the water chemistry of a recreational water facility, the method comprising:
   a. sensing one or more water chemistry values of water of the recreational water facility at a sensor pod;
   b. uploading the one or more chemistry values to a server, wherein the one or more chemistry values are uploaded to the server by the sensor pod;
   c. analyzing the one or more chemistry values by comparing the one or more sensed chemistry values against user set target chemistry values to obtain one or more analyzed chemistry values; and
   d. based upon the one or more analyzed chemistry values, sending from the server to a smart device a first message indicating that the chemistry values are within a targeted range and a second message indicating that the chemistry values are not within the targeted range, wherein the second message comprises one or more remedial steps to be applied to the water to normalize the chemistry values, and
   wherein the smart device communicates with the sensor pod to implement the remedial steps.

4. The method of claim 3, wherein the one or more chemistry values comprise one or more of pH, alkalinity, calcium hardness, chlorine levels, cyanuric acid, and temperature.

5. The method of claim 3, wherein the one or more sensed chemistry values are analyzed against a set of target chemistry values.

6. The chemistry monitoring system of claim 1, wherein the sensor pod is embedded within one of a water line and a pump line of the recreational water facility.

7. The method of claim 3, wherein the sensor pod is embedded within one of a water line and a pump line of the recreational water facility.

* * * * *